United States Patent [19]

Metz et al.

[11] 3,984,413
[45] Oct. 5, 1976

[54] PHENOXYALKANECARBOXYLIC ACID ESTERS OF HYDROXYALKYLTHEOPHYLLINES AND METHOD FOR THEIR MANUFACTURE

[75] Inventors: Gunter Metz, Blaubeuren; Manfred Specker, Ehingen (Danube), both of Germany

[73] Assignee: L. Merckle KG, Blaubeuren, Germany

[22] Filed: Feb. 21, 1974

[21] Appl. No.: 444,666

[30] Foreign Application Priority Data

Feb. 22, 1973 Germany............................ 2308826

[52] U.S. Cl.............................. 260/254; 424/253; 260/256
[51] Int. Cl.$^2$...................................... C07D 473/08
[58] Field of Search............................ 260/256, 254

[56] References Cited
FOREIGN PATENTS OR APPLICATIONS
1,106,327   5/1961   Germany ............................ 260/256

OTHER PUBLICATIONS

Finar, Organic Chemistry, vol. 1, pp. 175–176, pub. by Longmans, Green & Co., London, Third Ed. (1959).

Primary Examiner—Paul M. Coughlan, Jr.
Attorney, Agent, or Firm—Haseltine, Lake & Waters

[57]          ABSTRACT

Phenoxyalkanecarboxylic acids are esterified with 7-(2-hydroxyethyl) theophylline or 7-(2,3-dihydroxypropyl) theophylline. The resulting esters have excellent antilipemic and anticholesterolemic properties as well as pronounced peripheral and vasodilative effect.

12 Claims, No Drawings

PHENOXYALKANECARBOXYLIC ACID ESTERS OF HYDROXYALKYLTHEOPHYLLINES AND METHOD FOR THEIR MANUFACTURE

BACKGROUND OF THE INVENTION

A known phenoxyalkyl carboxylic ester having medicinal properties is ethyl 2-(p-chlorophenoxy) isobutyrate (Clofibrat).

The alcoholic components of the esters according to the invention and esters of their acid components are known from German specifications DT-AS 1,106,327 and DT-OS 1,695,355. These previously known compounds however, have only a delayed and deepened vascular effect serving for treatment of cardiovascular diseases, respiratory complaints and painful disorders of the biliary tracts, whereas the compounds in accordance with the invention display in addition their efficacy against lipemia and cholesterolemia. Furthermore, from German specification DT-OS 2,144,225 some salts are known which were formed from a basic theophylline derivative and Clofibrat. In these preparations, however, only the combined action of Clofibrat on the one hand and of the theophylline ingredients on the other is utilized, and nothing is stated in that disclosure as to a heightened efficacy against lipemia and cholesterolemia compared with Clofibrat.

SUMMARY OF THE INVENTION

The object of the invention is the preparation of new phenoxyalkane carboxylic acid esters of hydroxyalkyltheophyllines of the following formula (I)

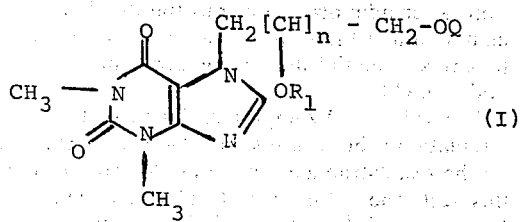

where $R_1$ is H or Q and Q is

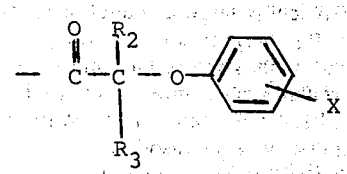

in which X represents halogen or trifluoromethyl; $R_2$ represents hydrogen, straight-chain or branched alkyl having 1 to 5 carbon atoms or halophenoxy; $R_3$ represents hydrogen or straight-chain or branched alkyl having 1 to 5 carbon atoms and n has the value zero or unity.

The halogen atoms comprise fluorine, chlorine, bromine and iodine atoms.

Examples of appropriate hydrocarbon radicals are alkyl radicals such as the methyl, ethyl, propyl, isopropyl, n-butyl, sec-butyl, tert-butyl or n-pentyl groups, and also branched pentyl groups. Alkyl radicals with 1 to 3 carbon atoms are preferred. The methyl group is especially preferred.

Preferred halophenoxyalkane carboxylic acid radicals have 1 to 7, preferably 1 to 5, carbon atoms in the alkanecarboxylic acid radical. Of the alkanecarboxylic acid radicals containing more than 2 carbon atoms, the branched ones are specially favored.

The invention further relates to a method for the preparation of phenoxyalkanecarboxylic acid derivatives of the general formula (I) wherein a phenoxyalkanecarboxylic acid of the general structure (II)

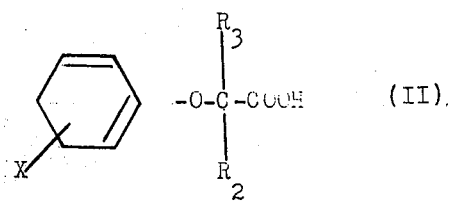

In which X, $R_2$ and $R_3$ are defined as before, or a reactive derivative of such acid is esterified with
a. 7-(2-hydroxyethyl) theophylline or
b. 7-(2,3-dihydroxypropyl) theophylline

DESCRIPTION OF PREFERRED EMBODIMENTS

Preferably the esterification is effected with the addition of a suitable catalyst such as hydrochloric acid, sulfuric acid, sulfuryl chloride or p-toluenesulfonic acid derivatives. Suitable acid derivatives are, for example, acid chlorides, acid anhydrides or esters. Instead of the alcohols (a) or (b), their reactive derivatives can equally well be used.

The direct reaction of the phenoxyalkanecarboxylic acid of the general structure (II) with the alcohol components takes place preferably in aromatic hydrocarbons at temperatures between 100° and 150°C whereby the water formed during the reaction can be removed azeotropically. The reaction can similarly be carried out in halohydrocarbons such as chloroform or ethylene dichloride, using sulfuric acid as a means of dehydration.

In all cases the solvent is preferably used in anhydrous form. The molar ratio between the alcohol components and the acid components in the reaction system ranges preferably from 1:1 to 1:3. The time for completion of the reaction amounts to 2 to 16 hours. After removal of acid and solvent residues, the resultant esters can be produced in pure form by suitable crystallization.

As was further surprisingly discovered, the production of the 2,3-dihydroxypropyltheophylline monoester by azeotropic esterification occurs selectively in superior yield.

Beside an excellent cholesterol and lipid lowering action, the phenoxyalkanecarboxylic acid esters of the general structure (I) have a pronounced peripheral and vasodilative effect. Compared with the known ethyl-2-(p-chlorophenoxy)-isobutyrate (Clofibrat) they display a substantially lower toxicity.

The following Table I shows the $LD_{50}$ values of compounds according to the invention compared to the median lethal dose of ethyl 2-(p-chlorophenoxy) isobutyrate, namely Clofibrat.

The acute toxicity of the preparations according to the invention was tested on CFJ strain mice and Sprague-Dawley rats.

The test substances according to Examples 2,5,6,8 and 10 were administered orally as a 5% suspension in methylcellulose by means of a probang, while the test material according to Example 4, was administered in a 8% gelatin suspension. The test materials for Examples 1 and 3 were administered orally by probang in an aqueous kaolin paste to rats (5 female and 5 male rats weighing 140 to 185 grams each).

The period of observation was 7 days. The experimental results were as follows:

TABLE I

| Test substance according to Example No. | Animal | $LD_{50}$ (mg/kg) |
|---|---|---|
| 1 | rat | >4000 |
| 2 | mouse | 2150 ** S = 1.09 (2060–2250) (1.06–1.12) |
| 3 | rat | >4000 |
| 4 | mouse | 1906 * |
| 5 | mouse | 1510 ** S = 1.09 (1440–1590) (1.06–1.12) |
| 6 | mouse | 1540 ** S = 1.25 (1370–1730) (1.18–1.33) |
| 8 | mouse | 2140 ** S = 1.07 (2070–2240) (1.05–1.09) |
| 10 | mouse | 1680 ** S = 1.14 (1500–1880) (1.11–1.17) |
| Comparison (Clofibrat) | mouse | 1150 Literature data |

* according to Spearman-Karber method
** According to Litchfield and Wilcoxon, using the Gaussian integral
S = slope ratio From this it appears that the $LD_{50}$ values of the compounds according to the invention are distinctly higher than those of the comparison preparation.

The antilipemic and anticholesterolemic action of the compounds according to the invention and of Clofibrat as a standard of comparison was tested on each of 10 male SPF Wistar strain rats of body weights from 80 to 90 g. For test purposes the animals were kept individually apart with restricted feed but water as desired. The animals of control group I were given 10 g basal diet daily, those of control group II, the test groups as well as the Clofibrat comparison group received in addition to the basal diet a fatty composition consisting of 40 g/kg butter with 5 g/kg cholesterol. The test substances conforming to the examples, and also the Clofibrat, were suspended in a 0.2% methylcellulose solution and administered by probang. The final cholesterol value and the value of the nonvolatile triglycerides was determined after 14 days treatment. The analyses were performed in the blood serum by means of an SMA 12/60 auto-analyzer. The results are summarized in Table II below. At this point it should be pointed out that a lowering of cholesterol by Clofibrat has frequently been reported in the literature, whereas in these experimental trials Clofibrat was absolutely inactive in this respect. The explanation for that is to be found in the paper by Berger et al. (Proc. Soc. Exp. Biol. Med. N.Y., 132: 293–297, 1969) from which it appears that in the fatty diet rat test, Clofibrat does not lower but even raises the cholesterol value.

The clinical pattern determined daily during the series of trials showed no differences in the over-all tolerance in the groups with test substances conforming to Examples 1, 2 and 3 as against the control groups and also the Clofibrat comparison group. Only in the test group conforming to Example 4 (100 mg/kg dosage) a reduced increase in weight was determined. There were no deaths. All of the groups displayed normal dental conditions; cornea, iris and crystalline lens were without deviation from normal conditions. No difference could be determined in hearing tests.

Table II

| Test Group | Dosage mg/kg | Final value cholesterol mg % | Drop % | Final value nonvolatile triglycerides | Drop % |
|---|---|---|---|---|---|
| Controls I | — | 80.1 ± 14.4 | — | 105.0 ± 15.0 | — |
| Controls II | — | 123.1 ± 14.4 | — | 135.7 ± 33.4 | — |
| Clofibrat | 133.3 | — | 107.7 | 20.6 ± 16.7 * | — |
| 250 | | ± 20.3 | | | |
| Ex. 1 | 100 | 95.2 ± 9.7 | 22.7 | 112.2 ± 32.1 | 17.3 |
| Ex. 2 | 100 | 130.3 ± 18.4 | — | 73.4 ± 48.7 ** | 45.9 |
| Ex. 3 | 100 | 122.0 ± 14.4 | — | 75.7 ± 39.3 ** | 44.2 |
| Ex. 4 | 35 | 132.3 ± 25.2 | — | 148.3 ± 58.6 | — |
| Ex. 4 | 100 | 111.0 ± 28.2 | 9.8 | 179.7 ± 130.8 | — |

* Statistical significance p <0.05
** Statistical significance p <0.01

The action on blood pressure and peripheral circulation was ascertained in trails on narcotized dogs, in which it was found that the compounds conforming to Examples 1, 2, 3 and 4 in accordance with the invention, after administration into the duodenum, did not acutely affect the systolic and diastolic blood pressure to any substantial degree for doses up to 200 mg/kg body weight.

According to Examples 2, 3 and 4, the peripheral circulation is increased some 20–30% of its initial level by the test substances according to those examples. In this test, the experimental substance conforming to Example 1 displayed only slight activity (up to 10%).

From the foregoing pharmacological trials it is apparent that the compounds according to the invention are superior to Clofibrat in that they have lower toxicity and also increased efficacy.

Thus in comparison to Clofibrat, the compounds of Examples 2 and 3 in a substantially lower dosage effect more than twice as large a reduction of the triglycerides, while the preparation according to Example 1 with comparatively good reduction of the triglycerides can with greater significance lower the increased cholesterol values. At the same time the preparations display a further favorable vasodilative effect without the blood pressure activity intrinsic to the alcoholic components of the preparations.

The drugs according to the invention contain one or more phenoxyalkanecarboxylic acid esters of the general structure (I) as active agent. Administration is preferably by mouth, in the for of capsules or tablets for example, which contain conventional pharmaceutical carriers and adjuvants if required.

Customary adjuvants for tablets are: starch, lactose, talc, magnesium or calcium stearate, microfine cellulose (Elcema); for tablet coating films: polymeric methacrylate coating such as Eudragit E soluble in gastric juice or Eudragit L/S insoluble in gastric juice; for capsules: starch, lactose, talc, microfine cellulose (Elcema G 250 and P 100); for suppositories: semisynthetic glycerides of vegetable fatty acids (Witespol, Massa Estarinlum); sedimentation retarders (Bentonite, aluminum stearate, glycerine stearate), builders (soyalecithin, Aerosil); for rectal capsules: vegetable oils, also hydrated vegetable oils as carriers, emulsifiers (Cremophor EL) and builders (waxes, soya lecithin) to impede sedimentation.

The production of the compounds according to the invention is illustrated in greater detail by the following examples:

EXAMPLE 1

107.3 g (0.5 mol) 2-(p-chlorophenoxy) isobutyric acid and 56.0 g (0.25 mol) 7-hydroxyethyltheophylline were suspended together in 250 ml xylene and heated for 15 hours in a water separator after addition of 1.5 g p-toluenesulfonic acid. The solution was next agitated with dilute sodium bicarbonate solution (0.5 mol $NaHCO_3$), waterwashed and evaporated in a rotary evaporator. The residue was crystallized from isopropanol, yielding 58.0 g (55% yield) 1-(7-theophyllinyl)-2-ethyl [2-(p-chlorophenoxy)-isobutyrate] with a melting point 131°–132°C.

| Elementary analysis: | | C | H | N | Cl |
|---|---|---|---|---|---|
| $C_{19}H_{21}ClN_4O_5$ | calc. | 54.23 | 5.03 | 13.31 | 8.42 |
| (420.8) | found | 54.14 | 4.95 | 13.50 | 8.31 |
| IR(KBr): | 1748, | 1704, | 1662/cm | | |

EXAMPLE 2

27.0 g (0.1 mol) 7-(2,3-dihydroxypropyl)-theophylline and 18.6 g (0.1 mol) p-chlorophenoxyacetic acid were heated in 100 ml xylene for 8 hours in a water separator with the addition of 0.9 g p-toluenesulfonic acid. After cooling down, the xylene was decanted and the residue dissolved in hot isopropanol. After addition of a little water the monoester crystallized out slowly. The yield was 33.4 g (79% yield) of 1-(7-theophyllinyl)-2-hydroxy-3-propyl (p-chlorophenoxyacetate) with a melting point of 81°–83°C.

| Elementary analysis: | | C | H | N | Cl |
|---|---|---|---|---|---|
| $C_{18}H_{19}ClN_4O_6$ | calc. | 51.13 | 4.53 | 13.26 | 8.38 |
| (422.8) | found | 51.01 | 4.66 | 13.07 | 8.23 |
| IR(KBr): | 3580, | 3475, | 1778, | 1705, | 1664/cm |

This composition still contained 2 – 3% moisture.

Recrystallization from methanol raised the melting point above 100°C. Thus, single crystallization from methanol yielded a composition with a melting point of 117°–118°C. Repeated crystallization from absolute methanol raised the melting point to 124.5°–126°C.

| Elementary analysis of the composition with m.p. 117–118°C | | | | | |
|---|---|---|---|---|---|
| | | C | H | N | Cl |
| $C_{18}H_{19}Cl N_4O_6$ | calc. | 51.13 | 4.53 | 13.26 | 8.38 |
| (422.8) | found | 51.07 | 4.48 | 13.11 | 8.32 |
| IR spectrum: | No bands at 3580/cm | | | | |
| NMR spectrum: | Only slight $HD_0$ signal; | | | | |

| Elementary analysis of the composition with m.p. 117–118°C | | | | |
|---|---|---|---|---|
| | C | H | N | Cl |
| Moisture after this, less than 0.5% | | | | |

Composition with m.p. 124.5°–126°C

The infrared spectrum shows no bands at 3580/cm with in other respects similar band distribution.

The nuclear magnetic resonance spectrum shows an HDO (heavy water) conversion signal less than 0.1% with in other respects similar signal distribution.

NMR spectrum (60 MHz/$CDCl_3$):

At $\delta$ = 3.66 and 3.56 ppm a definitely sharp singlet appears for the N—$CH_3$ protons (total 6 H); the methylene protons of the acid residue appear as a singlet at $\delta$ = 4.70 ppm (2H), and the remaining protons of the aliphatic side chain as a thickly widened singlet at $\delta$ = 4.28 ppm (6 H).

By reason of the comparison test, water of crystallization can be excluded. The moisture contained in the compounds cannot be removed in vacuo.

EXAMPLE 3

27.0 g (0.1 mol) 7-(2,3-dihydroxypropyl)-theophylline and 37.2 g (0.2 mol) p-chlorophenoxyacetic acid were heated in 200 ml xylene for 12 hours in a water separator after addition of 1.0 g p-toluenesulfonic acid. After standing overnight, the xylene solution was decanted and/or filtered and the residue crystallized from aqueous solution. There were obtained yield of 18.7 g (31.7%) 1-(7-theophyllinyl)-2,3-propylidenedi(p-chlorophenoxy acetate) with a melting point of 149°–150°C.

| Elementary analysis: | | C | H | N | Cl |
|---|---|---|---|---|---|
| $C_{26}H_{24}Cl_2N_4O_8$ | calc. | 52.80 | 4.09 | 9.47 | 11.99 |
| (591.4) | found | 52.87 | 3.99 | 9.58 | 11.97 |
| IR (KBr): | 1780, 1768, 1702, 1666/cm | | | | |

EXAMPLE 4

31.4 g (0.1 mol) bis-(p-chlorophenoxy)acetic acid and 11.2 g (0.05 mol) 7-hydroxyethyltheophylline were heated in 50 ml xylene for 6 hours in a water separator after addition of 0.3 g p-toluenesulfonic acid. The organic phase washed with $NaHCO_3$ solution and water was evaporated on the rotary evaporator and the residue crystallized from aqueous isopropanol. There were obtained 19.8 g (76.4 % yield) of 1-(7-theophyllinyl)-2-ethyl bis-(p-chlorophenoxy) acetate as a colorless crystallizate having a m.p. of 135°–136°C.

| Elementary analysis: | | C | H | N | Cl |
|---|---|---|---|---|---|
| $C_{23}H_{20}Cl_2N_4O_6$ | calc. | 53.20 | 3.88 | 10.79 | 13.65 |
| (519.3) | found | 53.34 | 3.83 | 10.84 | 13.71 |
| IR (KBr): | 1775, 1700, 1660, 1210, 835, 750cm | | | | |

EXAMPLES 5 THROUGH 11

Corresponding to the procedure of Example 1, with the use of the corresponding initial materials, further esters with $n = 0$ were prepared.

| Example | X | $R_2$ | $R_3$ | m.p.(°C) | Yield (%) |
|---|---|---|---|---|---|
| 5 | p-Cl | H | H | 120 | 76 |
| 6 | p-Cl | $CH_3$ | $CH_3$ | 116–118 | 78 |
| 7 | o-Cl | $CH_3$ | $CH_3$ | 136–138 | 67 |
| 8 | m-$CF_3$ | $CH_3$ | H | 128–130 | 62 |
| 9 | p-I | H | H | 134–136 | 37 |
| 10 | p-F | H | H | 115 | 78 |
| 11 | p-Br | H | H | 129 | 74 |

Pharmaceutical Preparations

The administration of the substances according to the invention is according to the particular case, per os or per rectum in daily doses of 100 to 1000 mg, preferably 100 to 500 mg, in the usual pharmaceutical forms with addition of customary carriers and binders. The following examples serve only as illustration and do not limit the invention.

EXAMPLE 12

Tablets
| | |
|---|---|
| Ester of Example 2 | 50 mg |
| Binder: Elcema P 100 | 50 mg |
| Lactose | 50 mg |
| Potato starch | 40 mg |
| Talc | 7 mg |
| Magnesium stearate | 3 mg |

EXAMPLE 13

Film-coated tablets
| | |
|---|---|
| Ester of Example 1 | 150 mg |
| Binder: Elcema P 100 | 80 mg |
| Lactose | 90 mg |
| Potato starch | 80 mg |
| Talc | 14 mg |
| Magnesium stearate | 6 mg |
| Coating lacquer: Eudragit L/S or E | |

EXAMPLE 14

Capsules
| | |
|---|---|
| a) Ester of Example 4 | 50 mg |
| Binder: Corn starch | 10 g |
| Lactose | 20 g |
| b) Ester of Example 1 | 200 mg |
| Binder: Corn starch | 15 mg |
| Lactose | 30 mg |

EXAMPLE 15

Suppositories
| | |
|---|---|
| Ester of Example 2 | 150 mg |
| Massa Estarinum BC appr. 5% glycerol monostearate | approx. 1950 mg |

EXAMPLE 16

Rectal Capsules (Rectocaps)
| | |
|---|---|
| Ester of Example 3 | 200 mg |
| Binder: Cremophor EL | 30 mg |
| Soya lecithin | 25 mg |
| Wax mixture | 180 mg |
| Vegetable oil | 360 mg |
| Partially hydrated vegetable oils | 121 mg |
| Gelatin coat: | gelatin, glycerol, ethyl- and propyl Parabens, coloring matter. |
| Outer coating: | Polyglycol 20000, Glycerol mono- and dioleate, Polyvinylacetate |

We claim:

1. A phenoxy alkane carboxylic acid ester of an hydroxyalkyltheophylline of the formula $$\text{(I)}$$

where $R_1$ is H or Q and Q is in which X represents halogen or trifluoromethyl; $R_2$ represents hydrogen, straight-chain or branched alkyl having 1 to 5 carbon atoms or halophenoxy; $R_3$ represents hydrogen or straight-chain or branched alkyl having 1 to 5 carbon atoms and n has the value zero or unity.

2. The ester of claim 1 where n is zero, $R_2$ and $R_3$ are $CH_3$ and X is p-Cl.
3. The ester of claim 1 where n is 1, $R_1$, $R_2$ and $R_3$ are H and X is p-Cl.
4. The ester of claim 1 where n is 1, $R_1$ is Q, $R_2$ and $R_3$ are H and X is p-Cl.
5. The ester of claim 1 where n is 0, $R_2$ is p-chlorophenoxy, $R_3$ is H and X is p-Cl.
6. The ester of claim 1 where n is 0, $R_2$ and $R_3$ are H and X is p-Cl.
7. The ester of claim 1 where n is 0, $R_2$ is $CH_3$, $R_3$ is H and X is p-Cl.
8. The ester of claim 1 where $n = 0$, $R_2$ and $R_3$ are $CH_3$ and X is o-Cl.
9. The ester of claim 1 where $n = 0$, $R_2$ is $CH_3$, $R_3$ is H and X is m-$CF_3$.
10. The ester of claim 1 where $n = 0$, $R_2$ and $R_3$ are H and X is p-I.
11. The ester of claim 1 where $n = 0$, $R_2$ and $R_3$ are H and X is p-F.
12. The ester of claim 1 where $n = 0$, $R_2$ and $R_3$ are H and X is p-Br.

* * * * *